United States Patent [19]

Wilke et al.

[11] Patent Number: 4,900,866
[45] Date of Patent: Feb. 13, 1990

[54] AZAPHOSPHOLENES

[75] Inventors: Günther Wilke; Jaroslaw Monkiewicz, both of Mülheim/Ruhr; Herbert Kuhn, Laumersheim, all of Fed. Rep. of Germany

[73] Assignee: Studiengesellschaft Kohle mbH, Mülheim/Ruhr, Fed. Rep. of Germany

[21] Appl. No.: 246,228

[22] Filed: Sep. 19, 1988

Related U.S. Application Data

[62] Division of Ser. No. 54,343, May 26, 1987, abandoned.

[30] Foreign Application Priority Data

May 26, 1986 [DE] Fed. Rep. of Germany ....... 3618169

[51] Int. Cl.⁴ .............................................. C07F 9/22
[52] U.S. Cl. .................................................. 564/13
[58] Field of Search ......................................... 564/13

Primary Examiner—Anton H. Sutto
Attorney, Agent, or Firm—Sprung Horn Kramer & Woods

[57] ABSTRACT

The invention relates to azaphospholenes of the type

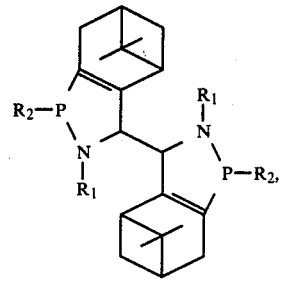

wherein $R_1$ and $R_2$ may be alkyl, aryl and aralkyl groups, processes for preparing same and the use thereof.

5 Claims, No Drawings

AZAPHOSPHOLENES

This is a division of application Ser. No. 054,343, filed May 26, 1987, now abandoned.

It has been known that olefins can be dimerized or co-dimerized by means of nickel-containing and phosphane-modified catalysts. Thus, the co-dimerization of cyclic dienes or strained olefins such as norbornene and ethene by using $\pi$-allylnickel halides or nickel (0) compounds and the activation thereof by means of Lewis acids and the modification with acyclic phosphanes, also optically active acyclic phosphanes, have been described several times [German Patent 20 39 125, Studiengesellschaft Kohle mbH. (priority 1970); U.S. Pat. No. 3,978,147, Studiengesellschaft Kohle mbH. (priority 1973); U.S. Pat. No. 4,098,834, Studiengesellschaft Kohle mbH. (priority 1976); G. Wilke et al., Angew. Chem. 1972, 1070; B. Bogdanovic et al., Angew. Chem. 1973, 1013; F. Petit et al., Bull. Soc. Chim. 1979, II-415; J. Chem. Soc. 1980, 937; G. Buono et al., J. Org. Chem. 1985, 50, 1781]. The processes known so far have technical disadvantages, as the catalysts show only relatively low activities and moreover, the accomplished selectivities are insufficient. The maximum numbers of catalytic cycles attainable with the processes described so far are too low for a commercial use.

Surprisingly, it was now found that said technical defects of the processes known so far can be overcome by using azaphospholenes as modifying ligands, the substituents of which azaphospholenes, due to their spatial requirements, will block certain rotations in the catalyst complexes. Therefrom ensue relatively rigid arrangements at the catalyst wherein always one nickel atom is complexed to each phosphorus atom. Such ligands are phospholenes having the following structure:

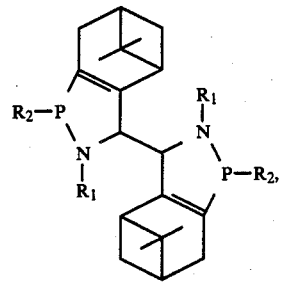

wherein the moieties $R_1$ and $R_2$ may be alkyl, aryl and aralkyl groups which may be varied within wide limits. Upon the preferred selection of

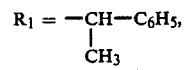

preferably in the optical R- or S-forms, respectively, and $R_2=CH_3$, particularly good results are obtained. The up to now unknown diastereomer built up with these substituents has the following structure and configuration according to x-ray structural analysis:

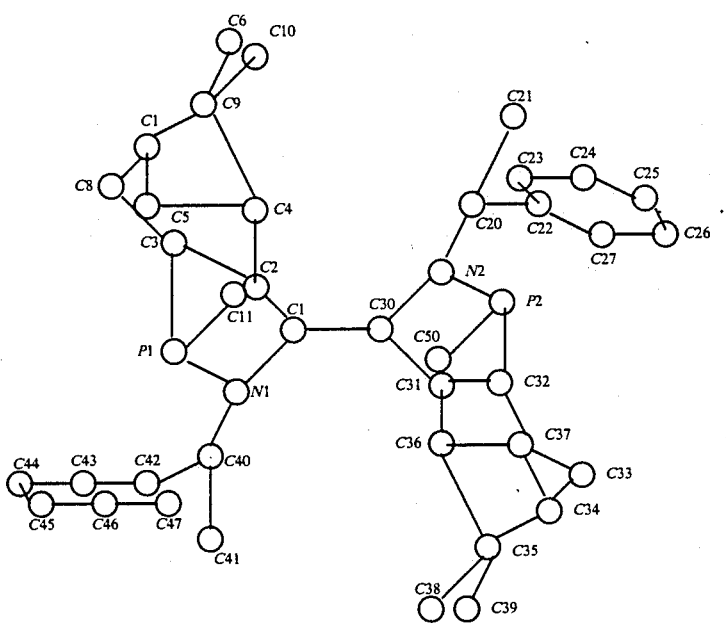

This diastereomer 6a was obtained by the following route starting from $(-)$-$\alpha$-pinene or $[(-)$-$(1R,5S)$-myrtenal 1] and $(+)$-R-$\alpha$-phenylethylamine 2.

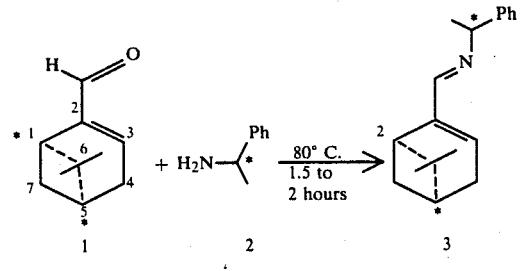

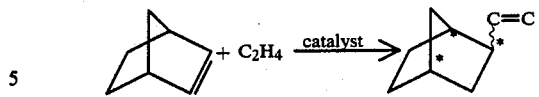

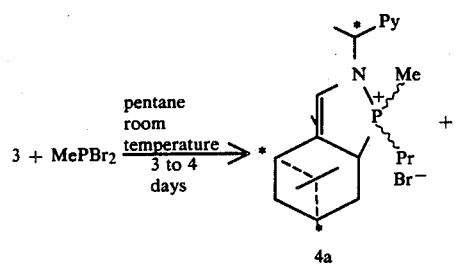

by the use of 6a as ligand in the nickel catalyst in $CH_2Cl_2$ has an enantiomeric excess (e.e.) of 57%, i.e. the ligand 6a causes not only high activity and selectivity, but also a high optical induction, so that according to the process an optically active product is obtained 78.5% of which consist of on enantiomer.

If, contrary thereto, an analogous phospholene is built up starting from (−)-α-pinene and (−)-S-α-phenylethylamine, then another diastereomer 6b results therefrom, the structure of which was also elucidated by X-ray analysis.

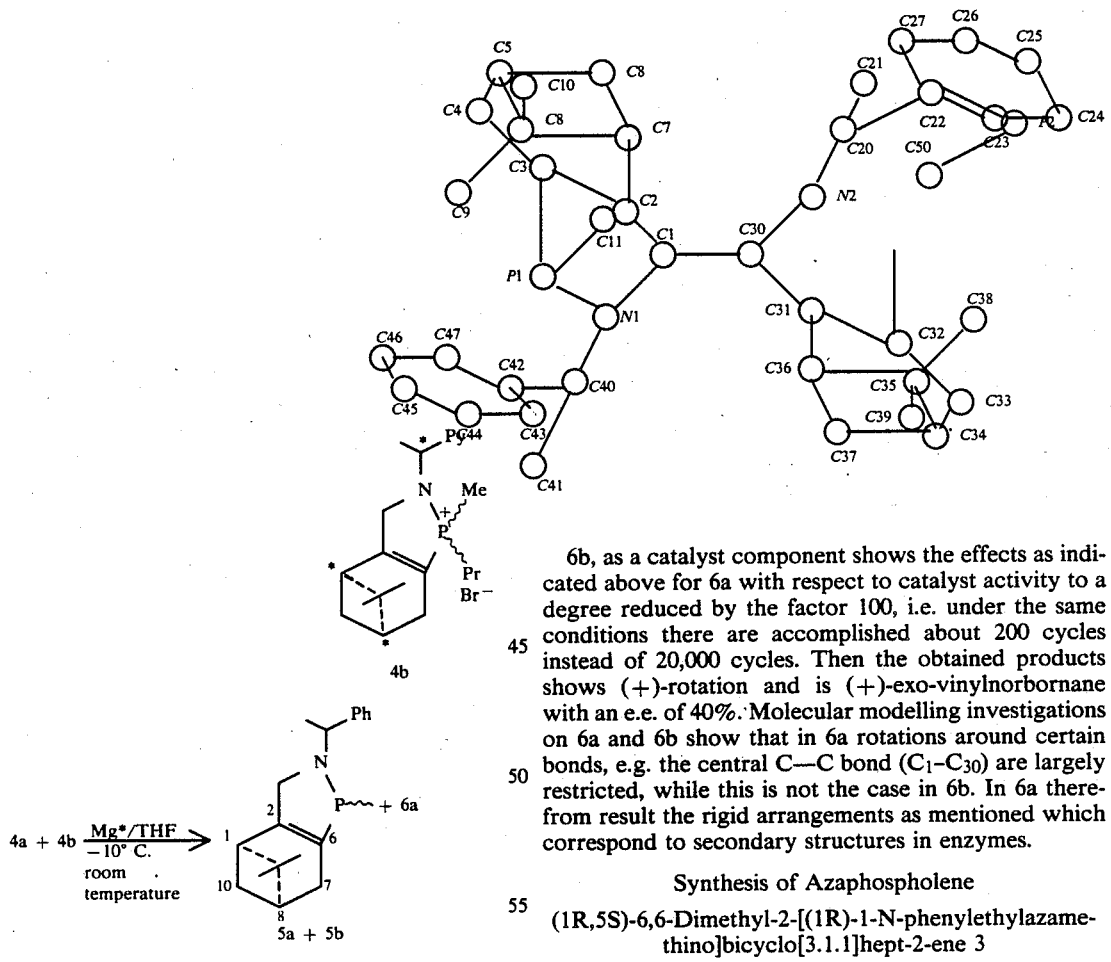

6b, as a catalyst component shows the effects as indicated above for 6a with respect to catalyst activity to a degree reduced by the factor 100, i.e. under the same conditions there are accomplished about 200 cycles instead of 20,000 cycles. Then the obtained products shows (+)-rotation and is (+)-exo-vinylnorbornane with an e.e. of 40%. Molecular modelling investigations on 6a and 6b show that in 6a rotations around certain bonds, e.g. the central C—C bond ($C_1$-$C_{30}$) are largely restricted, while this is not the case in 6b. In 6a therefrom result the rigid arrangements as mentioned which correspond to secondary structures in enzymes.

In an analogous manner, starting from (+)-α-pinene and (−)-S-α-phenylethylamine there may be prepared the compound 6a' which is the enantiomer of the aforementioned diastereomer. 6a and 6a' as ligands in nickel-containing catalysts have the effect that, e.g., the co-dimerization of norbornene with ethene may be realized even at a temperature of from +60° C. to −120° C., and preferably of from −20° C. to −80° C., with an activity of 20,000 cycles per hour and selectivities of >90%. The (−)-exo-vinylnorbornane formed according to the following reaction equation Synthesis of Azaphospholene (1R,5S)-6,6-Dimethyl-2-[(1R)-1-N-phenylethylazamethino]bicyclo[3.1.1]hept-2-ene 3

34.37 g (0.284 mol) of (+)-(1R)-phenylethylamine 2 are charged in a 250 ml flask and heated to 70°–80° C. At this temperature 42.94 g (0.286 mol) of (−)-(1R,5S)-myrtenal 1 are dropwise added within 1 h. A two-phase mixture is formed stirring of which is continued for 1 h. After cooling to room temperature 50 ml of ether are added, the aqueous phase is separated (4 ml), and the organic phase is dried with $KOH/Na_2SO_4$. Then the ether is condensed off, and the crude product 3 is distilled under high vacuum.

Yield: 62.3 g (86.7% of theory); b.p. 108°–112° C.

5-Bromo-5,9,9-trimethyl-4-[(1R)-1-phenylethyl]-4-aza-5-λ⁴-phosphoniatricyclo-[6.1.1¹·⁸,0²·⁶]-dec-2(3)-ene bromide 4a, 5-Bromo-5,9,9-trimethyl-4-[(1R)-1-phenylethyl]-4-aza-5-λ⁴-phosphoniatricyclo-[6.1.1¹·⁸,0²·⁶]-dec-2(6)-ene bromide 4b 49.40 g (0.195 mol) of the azadiene 3 in 700 ml of n-pentane are charged, and 40.14 g (0.195 mol) of MePBr₂ is about 200 ml of n-pentane are dropwise added. A yellow precipitate is immediately formed. After the MePBr₂ addition, the reaction mixture is stirred for 4 days. Then the yellow solid (crude phosphonium salts 4) are filtered off, washed three times with 100 ml of n-pentane each and dried in vacuo.

Yield of crude material: 75.1 g (84.0% of theory).

($\delta$) $^{31}$p-NMR: 4a 77.2 ppm (CD$_2$Cl$_2$); 4b 67.1 ppm (CD$_2$Cl$_2$).

Bis-(3R)-3-{(1R,5R,8R)-5,9,9-trimethyl-4-[(1R)-1-phenylethyl]-4-aza-5-phosphatricyclo-[6.1.1$^{1.8}$,0$^{2.6}$]-dec-2(6)-enyl} 6a 10.05 g (21.9 mmol) of the crude product 4 are suspended in 100 ml of THF on a frit, the filtrate is collected in a flask, and the residue is discarded. To the orange-colored filtrate there are added at −10° C. 0.66 g (272 mmol) of active magnesium portionwise under vigorous stirring. After the completion of the addition the batch is allowed to warm up slowly to room temperature and is stirred overnight. After the solvent has been condensed off, 200 ml of ether are added to the residue, and the mixture is filtered. The ether is condensed off from the yellow filtrate to obtain 10.62 g of a viscous residue which is dissolved in 4 to 5 parts by volume of methanol with heating to about 60° C. In a water bath (about 60° C.) the mixture is stirred and allowed to cool to room temperature overnight. A colorless precipitate of 6a is formed.

Yield: 0.84 g (12.9% of theory); m.p. 134°–135° C. (recrystallized from ethanol).

($\delta$) $^{31}$P-NMR: 49.9 ppm (toluene); $[\alpha]^{589} = -64.69°$ (0.64 g/100 ml of CH$_2$Cl$_2$).

The azaphospholenes of the type 6a are suitable for the preparation of catalysts of a highly selective activity which in turn are capable of converting unsaturated hydrocarbons into optically active compounds. Thus, an optically active vinyl bicycloheptane is obtained from bicycloheptene and ethylene in space-time yields not yet described so far. Said optically active vinyl bicycloheptane in turn may be the starting material for the terpolymerization together with, e.g., ethylene and propylene to give polymers, and more particularly optically active polymers. Optically active polymers, due to their high sterical regularity, have improved physical and mechanical properties. Thus, optically active polymers are suitable as absorbents for the separation of enantiomers. In the same manner, an optically active 3-phenylbutene-1 is selectively obtainable in high yield from styrene and ethylene by co-dimerization, and so are substituted 3-phenylbutenes-1 from substituted styrenes and ethylene. The polymerization of this α-olefin products to optically active polymers is effected in the same way as the terpolymerization set forth above.

A further application of the azaphospholenes in the form of the described complex compounds together with organoaluminum compounds is the selective change of the structure of, e.g., heptadiene-1,6 to form 1-methyl-2-methylidene-cyclopentene, as well as the co-dimerization of 1,3-cyclopentadiene and ethylene leading to optically active 3-phenylpentene-1.

Catalytic Synthesis of Vinyl Bicycloheptane

EXAMPLE 1

A 2-1 four-neck flask equipped with stirrer, dropping funnel and a Claisen head with thermometer is evacuated with heating and filled with argon. The flask is charged with 600 ml of CH$_2$Cl$_2$, and the dropping funnel is filled with 600 ml of a CH$_2$Cl$_2$ solution of 400 g (4.25 mol) bicyclo[2.2.1]heptene. The flask is cooled to −65° C. while its content is stirred, and 0.047 g (0.108 mmol) of π-allylnickel chloride/phosphane 6a complex (Ni:P=1:1) dissolved in about 10 ml of cooled CH$_2$Cl$_2$ and 0.239 ml (1 mmol) of Et$_3$Al$_2$Cl$_3$ (P:Ni:Al=1:1:20) are added, whereupon the complex solution becomes violet in color. After briefly evacuating with an oil pump, the vacuum is removed with dry ethylene, and the solution of bicycloheptene is dropwise added with stirring within 60 minutes. In the course thereof a high heat evolution is observed. During the reaction period (90 minutes) ethylene is introduced into the apparatus whereby the reaction temperature is increased to −58° C.

Then the reaction is terminated by introducing gaseous ammonia, and the product is condensed off in vacuo. From the condensate thus obtained the solvent is distilled off under normal pressure, and the residue is distilled through a Vigreux column.

Yield: 384 g (74% of theory).

(−)-exo-2-vinyl bicyclo[2.2.1]heptane (54% e.e.); conversion number: 29,140.

$[\alpha]_{max}^{22} = (+) 51°$; b.p. 54° C./30 mbar;
$D^{20} = 0.8726$ g/cm$^3$.

EXAMLE 2

The procedure is as in Example 1, using a 0.5-1 four-neck flask. The flask is charged with 150 ml of CH$_2$Cl$_2$, and the dropping funnel is filled with 30 ml (0.32 mol) of bicyclo[2.2.1]heptene in 50 ml of CH$_2$Cl$_2$. The solvent is cooled to −70° C., and 0.0961 g (0.352 mmol) of bis-cyclooctadienenickel and 0.105 g (0.352 mmol) of the phosphane 6a are added. The reaction mixture is allowed to warm up slowly to −15° C., until a strongly yellow clear solution is formed, and then is again cooled to −70° C., and 0.080 ml (0.352 mmol) of Et$_3$Al$_2$Cl$_3$ (P:Ni:Al=1:1:2) are added. After renewed heating to −20° C. the solution is saturated with ethylene, and the solution of bicycloheptene is dropwise added within 15 minutes. The reaction mixture is kept saturated with ethylene by vigorous stirring for 60 minutes. The reaction is terminated with gaseous ammonia. The product is condensed off, the solvent is withdrawn, and the residue is distilled through a Vigreux column about 30 cm in length.

Yield: 35 g (90% of theory).

(−)-exo-2-vinyl bicyclo[2.2.1]heptane (8.2% e.e.); conversion number: 815.

EXAMPLE 3

The procedure is as in Example 1. A 1-liter flask is charged with 500 ml of chlorobenzene, and the dropping funnel is filled with 30 g (0.32 mol) of bicycloheptene in 50 ml of chlorobenzene. The chlorobenzene is stirred and cooled to −40° C., and 0.090 g (0.186 mmol) of π-allylnickel/phosphane-6a complex in about 15 ml of cooled chlorobenzene and 0.135 g (1.12 mmol) of Et$_2$AlCl (P:Ni:Al=1:1:6) are added thereto. Then the solution of bicycloheptene is dropwise added within about 15 minutes, and ethylene is introduced into the apparatus. In the course of 2 h the reaction mixture is heated to +40° C.

The catalysis is terminated by introducing gaseous ammonia, and the product is condensed off in vacuo. From the condensate thus obtained the solvent is distilled off under normal pressure, and the residue is distilled through a Vigreux column.

Yield: 34 g (87.5% of theory).
(+)-exo-2-vinyl bicyclo[2.2.1]heptane (10.8% e.e.); conversion number: 1498. Thus, in chlorobenzene the formation of the (+)-form is preferred.

EXAMPLE 4

The procedure is as in Example 1. A 0.5-1 flask is charged with 150 ml of CHCl$_3$, and the dropping funnel is filled with 30 g (0.32 mol) of bicycloheptene in 50 ml of CHCl$_3$. The solvent is cooled to −30° C., and 0.020 g (0.114 mmol) of nickel acetate and 0.0678 g (0.228 mmol) of phosphane 6a are added. The reaction mixture is stirred for 30 minutes at −30° C., and then 0.133 g (0.684 mmol) of AgBF$_4$ (P:Ni:BF$_4$=2:1:6) are added. After stirring for another 30 minutes the solution of bicycloheptene is dropwise added within 10 minutes, and ethylene is simultaneously introduced into the apparatus. After 60 minutes the reaction is terminated by introducing gaseous ammonia. The product is condensed off, the solvent is withdrawn, and the residue is distilled.

Yield: 32 g (85% of theory).
(−)-exo-2-vinyl bicyclo[2.2.1]heptane (29% e.e.); conversion number: 2300.

EXAMPLE 5

The procedure is an in Example 1. A 0.5-1 flask is charged with 150 ml of CH$_2$Cl$_2$, and the dropping funnel is filled with 15 g (0.16 mol) of bicycloheptene. The solvent is stirred and cooled to −72° C., and 0.287 g (0.66 mmol) of π-allylnickel/phosphane-6b complex in about 20 ml of cooled CH$_2$Cl$_2$ and 0.150 ml (0.66 mmol) of Et$_3$Al$_2$Cl$_3$ (P:Ni:Al=1:1:2) are added thereto, whereby the complex solution becomes violet in color. Then at −72° C. the solution of bicycloheptene is dropwise added within 30 minutes, and ethylene is simultaneously introduced into the solution. Upon completion of the bicycloheptene addition, the introduction of ethylene is continued for another 30 min. The reaction is terminated by introducing gaseous ammonia, and the product is condensed off in vacuo, the solvent is withdrawn, and the residue is distilled.

Yield: 18 g (92% of theory).
(+)-exo-2-vinyl bicyclo[2.2.1]heptane (38% e.e.); conversion number: 224.

EXAMPLE 6

The procedure is as in Example 1. A 0.5-1 flask is charged with 150 ml of CH$_2$Cl$_2$, and the dropping funnel is filled with 18 g (0.19 mol) of bicycloheptene in 20 ml of CH$_2$Cl$_2$. The solvent is stirred and cooled to −30° C., and 0.283 g (0.946 mmol) of the mixture of the phosphane isomers 5a and 5b and 0.128 g (0.473 mmol) of bis-π-allylnickel chloride are added. The reaction mixture is stirred for 30 minutes and then cooled to −70° C., and 0.454 ml (1.892 mmol) of Et$_3$Al$_2$Cl$_3$ (P:Ni:Al=1:1:4) are added thereto. After briefly evacuating with an oil pump, the vacuum is removed with dry ethylene, and the solution of bicycloheptene is dropwise added within 15 minutes. Then the introduction of ethylene into the apparatus is continued for another 15 min. The reaction is terminated by introducing gaseous ammonia, the product is condensed off in vacuo, the solvent is withdrawn, and the residue is distilled.

Yield: 6 g (26% of theory). (−)-exo-2-vinyl bicyclo[2.2.1]heptane (3.4% e.e.);
conversion number: 52.

EXAMPLE 7

The procedure is as in Example 1. A 0.5-1 flask is charged with 150 ml of CH$_2$Cl$_2$, and the dropping funnel is filled with 30 g (0.32 mol) of bicycloheptene in 50 ml of CH$_2$Cl$_2$. The solvent is cooled to −65° C., and 0.086 g (0.197 mmol) of π-allylnickel chloride/phosphane-6a complex dissolved in 10 ml of cooled CH$_2$Cl$_2$ and 0.227 ml of Et$_3$Al$_2$Cl$_3$ are added. The reaction mixture ist stirred at −65° C. for 15 minutes. Then 0.118 g (0.394 mmol) of the phosphane 6a (P:Ni:Al=3:1:10) are added, and the solution is stirred for another 10 minutes. Then the solution of bicycloheptene is dropwise added within 15 minutes, and ethylene is simultaneously introduced into the apparatus. The reaction is terminated by introducing gaseous ammonia, the product is condensed off in vacuo, the solvent is withdrawn, and the residue is distilled.

Yield: 34 g (87% of theory).
(−)-exo-2-vinyl bicyclo[2.2.1]heptane (57% e.e.); conversion number: 1413.

EXAMPLE 8

A 100-1 glass reaction vessel equipped with stirrer, a 25-1 feed tank and an internal thermometer is provided with an argon atmosphere. The reaction vessel is charged with 50 l of CH$_2$Cl$_2$, and the feed tank is filled with 10.13 kg (107.7 mol) of bicycloheptene in 10 l of CH$_2$Cl$_2$. The charged solvent is cooled to −40° C. by means of a refrigerating machine, and the bicycloheptene solution is cooled to −13° C.

Then ethylene is introduced, and 23 ml (0.102 mol) of Et$_3$Al$_2$Cl$_3$ and 4.448 g (0.0127 mol) of π-allylnickel chloride/phosphane-6a complex dissolved in 50 ml of CH$_2$Cl$_2$ (P:Ni:Al=1:1:20) are added. Then, with simultaneous introduction of ethylene, the solution of bicycloheptene is allowed to run in within 6 hours. With full output of the connected refrigerating machine the reaction temperature increases to −31° C. After 6.5 h the reaction is terminated by the introduction of gaseous ammonia. Then the solvent is distilled off under normal pressure, and the residue is fractioned through a column.

Yield: 8.0 kg (65.6 mol; 60.9% of theory)
(−)-exo-2-vinyl bicyclo[2.2.1]heptane (32.6% e.e.); conversion number: 6388.

Catalytic Synthesis of Optically Active 3-Phenylbutene-1

EXAMPLE 9

A 2-1 four-neck flask equipped with stirrer, dropping funnel and a Claisen head with thermometer is evacuated with heating and filled with argon. The flask is charged with 700 ml of CH$_2$Cl$_2$, and the dropping funnel is filled with 460 ml of a CH$_2$Cl$_2$ solution cooled to −30° C. of 275 g (2.65 mol) of styrene. The flask is cooled to −70° C. while its contact is stirred, and 0.590 g (1.36 mmol) of π-allylnickel chloride/phosphane 6a complex (Ni:P=1:1) dissolved in about 15 ml of cooled CH$_2$Cl$_2$ and 0.70 ml (3.0 mmol) of Et$_3$Al$_2$Cl$_3$ (P:Ni :Al=1:1:3) are added. After briefly evacuating with an oil pump, the vacuum is removed with dry ethylene, and the solution of styrene is dropwise added with stirring within 45 minutes. In the course thereof the solution becomes warmed up to −60° C. During the reaction period (150 minutes) ethylene is introduced into the apparatus. The catalysis is terminated by introducing gaseous ammonia, and the product is condensed off in vacuo. From the condensate thus obtained the solvent is distilled off under normal pressure, and the residue is distilled through a Vigreux column. Yield: 340 g (97% of theory).

(−)-(R)-3-phenylbutene-1 (93% e.e.);
conversion number: 1890.

EXAMPLE 10

The procedure is as in Example 1, using a 0.5-1 four-neck flask. The flask is charged with 150 ml of $CH_2Cl_2$, and the dropping funnel is filled with 18 g (0.17 mol) of styrene in 30 ml of $CH_2Cl_2$. The solvent is cooled to −70° C., and 0.0553 g (0.13 mmol) of $\pi$-allylnickel chloride/phosphane 6a complex in about 15 ml of cooled $CH_2Cl_2$ and 0.030 ml (0.13 mmol) of $Et_3Al_2Cl_3$ are added. Thereafter the reaction mixture is warmed up to 0° C. within 60 minutes. At 0° C. the solution of styrene is dropwise added within 15 minutes, and ethylene is introduced into the apparatus. The reaction is terminated by introducing gaseous ammonia, and the product is condensed off in vacuo. Then, the solvent is withdrawn, and the residue is distilled. Yield: 20.9 g (93% of theory).

(−)-(R)-3-phenylbutene-1 (76% e.e.);
conversion number: 1216.

EXAMPLE 11

The procedure is as in Example 1, using a 0.5-1 four-neck flask. The flask is charged with 150 ml of toluene, and the dropping funnel is filled with 20 g (0.19 mol) of styrene in 40 ml of toluene. At room temperature 0.120 g (0.44 mmol) of bis-cyclooctadienenickel and 0.131 g (0.44 mmol) of the phosphane 6a are added. The reaction mixture is stirred for 30 minutes, and then 0.106 g (0.88 mmol) of $Et_2AlCl$ (P:Ni:Al=1:1:4) are added. Then the solution of styrene is dropwise added within 30 minutes, and ethylene is introduced into the apparatus. By way of vigorous stirring the reaction mixture is kept saturated with ethylene for 4 hours. The catalysis is terminated by the addition of ethanol, and the product is condensed off in vacuo. From the condensate the solvent is distilled off through a Vigreux column under normal pressure, and the residue is fractionated under vacuum.

Yield: 15.1 g (60.2% of theory).
(−)-(R)-3-phenylbutene-1 (53% e.e.);
conversion number: 260.

EXAMPLE 12

The procedure is as in Example 1. A 0.5-1 flask is charged with 150 ml of $CH_2Cl_2$, and the dropping funnel is filled with 20.3 g (0.195 mol) of styrene in 20 ml of $CH_2Cl_2$. The solvent is cooled to −60° C. with stirring, and 0.0529 g (0.122 mmol) of $\pi$-allylnickel bromide/phosphane 6a in 20 ml of cooled $CH_2Cl_2$ and 0.028 ml (0.122 mmol) of $Et_3Al_2Cl_3$ (P:Ni:Al=1:1:2) are added. After warming up to room temperature (+20° C.) the catalyst solution is saturated with ethylene, and the solution of styrene is dropwise added within 15 minutes. The reaction mixture is kept in contact with ethylene by vigorous stirring for 30 minutes. Then the reaction is terminated by introducing gaseous ammonia, and the product is condensed off in vacuo. From the condensate thus obtained the solvent is withdrawn, and the residue is distilled.

Yield: 24.7 g (96% of theory).
(+)-(S)-3-phenylbutene-1 (70% e.e.);
conversion number: 1533.

EXAMPLE 13

The procedure is as in Example 1. A 0.5-1 flask is charged with 150 ml of $CH_2Cl_2$, and the dropping funnel is filled with 20 g (0.196 mol) of styrene in about 30 ml of $CH_2Cl_2$. The solvent is cooled to −30° C., and 0.050 g (0.286 mmol) of nickel acetate and 0.086 g (0.286 mmol) of phosphane 6a are added. The reaction mixture is stirred at −30° C. for 60 minutes, and then 0.222 g (1.144 mmol) of $AgBF_4$ are added (P:Ni:$BF_4$=1:1:4). After another 30 minutes of stirring the solution of styrene is dropwise added within 20 minutes, and ethylene is simultaneously introduced into the apparatus. After 60 minutes, the reaction is terminated by introducing gaseous ammonia, the product is condensed off in vacuo, the solvent is withdrawn, and the residue is distilled through a Vigreux column.

Yield: 12 g (46% of theory).
(−)-(R)-3-phenylbutene-1 (75% e.e.);
conversion number: 317.

Catalytic Synthesis of Optically Active
1-Methyl-2-methylidenecyclopentene

EXAMPLE 14

The procedure is as in Example 1 using a 0.5-1 four-neck flask. The flask is charged with about 150 ml of $CH_2Cl_2$, and the dropping funnel is filled with 10 g (0.104 mol) of heptadiene-1,6 in about 20 ml of $CH_2Cl_2$. The solvent is cooled to −30° C., and 0.079 g (0.182 mmol) of $\pi$-allylnickel chloride/phosphane 6a complex in 15 ml of cooled $CH_2Cl_2$ and 0.045 ml (0.197 mmol) of $Et_3Al_2Cl_3$ are added. The solution becomes orange in color. The catalyst mixture is stirred at −30° C. for 30 minutes, and then the solution of heptadiene-1,6 is dropwise added within 15 minutes. After 3 hours at −30° C. the reaction is stopped with gaseous ammonia. The crude product is condensed off in vacuo, the solvent is withdrawn, and the residue is distilled through a Vigreux column.

Yield: 9.4 g (94% of theory).
1-(S)-(+)-1-methyl-2-methylidenecyclopentene,
b.p. 96° C.; $[\alpha]_D^{22}$ +61.6° (undiluted) (93% e.e.);
conversion number: 1540

EXAMPLE 15

A 100 l glass reaction vessel equipped with stirrer, a 25-1 feed tank and an internal thermometer is provided with an argon atmosphere. The reaction vessel is charged with 40 l of $CH_2Cl_2$, and the feed tank is filled with 8.26 kg (79.5 mol) of styrene cooled to −20° C. in 16 l of $CH_2Cl_2$. The charged solvent is cooled to −62° C. by means of a refrigerating machine. The liquid is stirred, while 20.3 g (0.047 mol) of $\pi$-allylnickel chloride/phosphane 6a complex dissolved in 100 ml of $CH_2Cl_2$ cooled to −60° C. and 25 ml (0.109 mol) of $Et_3Al_2Cl_3$ (P:Ni:Al=1:1:4.6) are added. Then ethylene is introduced, and the solution of styrene cooled to −20° C. by means of a second refrigerating machine is allowed to run in within 6 hours. The reaction temperature is maintained within a range of from −60° C. to −65° C. After 7 hours the reaction is terminated by the introduction of gaseous ammonia. The solvent is distilled off under normal pressure, and the residue is fractioned through a column.

Yield: 4.3 kg (32.5 mol; 41% of theory; 87.4% e.e.).
(−)-(R)-3-phenylbutene-1; conversion number: 691.

EXAMPLE 16

The procedure is as in Example 1. A 0.5-1 flask is charged with 150 ml of $CH_2Cl_2$, and the dropping funnel is filled with 10 g (0.085 mol) of 4-methylstyrene in about 40 ml of $CH_2Cl_2$. The solvent is cooled to −70° C. with stirring, and 0.109 g (0.25 mmol) of $\pi$-allylnickel/phosphane 6a complex in about 20 ml of $CH_2Cl_2$ and 0.115 ml (0.50 mmol) of $Et_3Al_2Cl_3$ (P:Ni:Al=1:1:4) are added. At −70° C. the solution of 4-methylstyrene is dropwise added within 15 minutes, and ethylene is simultaneously introduced into the solution. The reaction is terminated by introducing gaseous ammonia, and the reaction mixture is condensed off in vacuo. The solvent is withdrawn, and the residue is distilled in vacuo.

Yield: 11.7 g (94.4% of theory).
(−)-(R)-p-tolylbutene-1);
conversion number: 320; $[\alpha]_D^{22}$ −9.89° in substance (95.2% e.e.).

EXAMPLE 17

The procedure is as in Example 1. A 0.5-1 flask is charged with 150 ml of $CH_2Cl_2$, and the dropping funnel is filled with 16 g (0.242 mol) of monomeric cyclopentadiene-1.3 in 15 ml of cooled $CH_2Cl_2$. The solvent is cooled to −70° C., and 1.22 g (2.81 mmol) of $\pi$-allylnickel/phosphane 6a complex in 25 ml of cooled $CH_2Cl_2$ and 0.353 ml (2.81 mmol) of $Et_2AlCl$ are added (P:Ni:Al=1:1:1). The reaction mixture is stirred at −70° C. for 30 minutes. Then ethylene is introduced into the apparatus for 1 minute, and then the solution of cyclopentadiene-1,3 is slowly added dropwise with simultaneous introduction of ethylene. The addition of the cyclopentadiene-1,3 solution takes 1 hour. Then the reaction mixture was stirrend for another hour. The reaction is terminated by introducing gaseous ammonia, and the product is condensed off in vacuo. The solvent is withdrawn, and the residue is distilled.

Yield: 8 g (0.084 mol; 35% of theory).
(−)-(R)-3-vinylpentene-1 (92% e.e.);
conversion number: 30.

We claim:

1. An azaphospholene of the formula

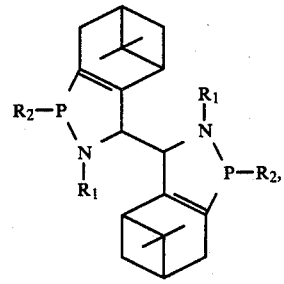

wherein $R_1$ and $R_2$ each independently is lower alkyl, aryl or aralkyl.

2. An azaphospholene according to claim 1, wherein $R_1$ and $R_2$ each independently is lower alkyl, phenyl or phenyl-lower alkyl.

3. An azaphospholene according to claim 1, wherein $R_1$ and $R_2$ each independently is methyl or phenylethyl.

4. Bis-(3R)-3-{(1R,5R,8 R)-5,9,9-trimethyl-4-[(1R)-1-phenylethyl]-4-aza-5-phosphatricyclo-[6.1.1$^{1.8}$.0$^{2.6}$]-dec-2(6)-enyl}.

5. A process for preparing bis-(3R)-3-((1R,5R,8R)-5,9,9-trimethyl-4-[(1R)-1-phenylethyl]-4-aza-5-phosphatricyclo-[6.1.1$^{1.8}$.0$^{2.6}$]-dec-2(6)-enyl), comprising reacting phenylethylamine and myrtenal at about 70° to 80° C. to obtain (1R,5S)-6,6-dimethyl-2-[(1R)-1-N-phenylethyl-azamethino]bicyclo[3.1.1]hept-2-ene, reacting that compound in a second step with methyldibromophosphane to form 5-bromo-5-5,9,9-trimethyl-4-[(1R)-1-phenylethyl]-4-aza-5-$\lambda^4$-phosphoniatricyclo-[6.1.1$^{1.8}$.0$^{2.6}$]-dec-2(6)-ene bromide, and treating such product in the cold with excess active magnesium.

* * * * *